US00PP36699P2

(12) United States Plant Patent
Johnson, Jr.

(10) Patent No.: US PP36,699 P2
(45) Date of Patent: May 20, 2025

(54) ***BEGONIA* PLANT NAMED 'Little Moon'**

(50) Latin Name: ***Begonia* hybrid**
Varietal Denomination: Little Moon

(71) Applicant: Ozzie W. Johnson, Jr., Marietta, GA (US)

(72) Inventor: Ozzie W. Johnson, Jr., Marietta, GA (US)

( * ) Notice: Subject to any disclaimer, the term of this patent is extended or adjusted under 35 U.S.C. 154(b) by 0 days.

(21) Appl. No.: 18/944,063

(22) Filed: Nov. 12, 2024

(51) Int. Cl.
*A01H 5/02* (2018.01)
*A01H 6/18* (2018.01)

(52) U.S. Cl.
USPC ..... Plt./343
CPC ..... *A01H 6/185* (2018.05)

(58) Field of Classification Search
USPC ..... Plt./343
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Begonia* plant named 'Little Moon' is disclosed, characterized by its dark green foliage mottled with silver. Plants exhibit root hardiness, small leaf size and rhizomatous spreading. Flowers are light pink with darker pink flower buds. The new cultivar is a *Begonia*, typically suited for garden and ornamental container use.

2 Drawing Sheets

Latin name of the genus and species: *Begonia* hybrid.
Cultivar denomination: 'Little Moon'.

BACKGROUND OF THE INVENTION

The new cultivar is a product of a planned breeding program. The new cultivar originated from an open-pollination of various *Begonia* species and cultivars by the inventor during 2012. The crossing was made in Marietta, GA in the inventor's garden.

'Little Moon' was selected by the inventor, in 2013 Marietta, GA in the inventor's garden.

After selection of the new cultivar, asexual reproduction of 'Little Moon' was first performed at the inventor's home by leaf cuttings in 2014. 'Little Moon' has since produced several generations and has shown that the unique features of this cultivar are stable and reproduced true to type.

SUMMARY OF THE INVENTION

The cultivar 'Little Moon' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Little Moon'. These characteristics in combination distinguish 'Little Moon' as a new and distinct *Begonia* cultivar:

1. Dark green foliage mottled with silver.
2. Root hardiness.
3. Small leaf size.
4. Light pink flower and darker pink flowers buds.
5. Rhizomatous spreading.

PARENTAL COMPARISON

Exact parentage cannot be identified.

COMMERCIAL COMPARISON

Plants of the new cultivar 'Little Moon' are similar to the commercial cultivar 'Sterling Moon', U.S. Plant Pat. No. 33,164 in most horticultural characteristics. However, 'Little Moon' differs in the following:

1. The new cultivar is about ⅓ the size of 'Sterling Moon'.
2. The new cultivar has smaller sized flowers and foliage.

Plants of the new cultivar 'Little Moon' are similar to the commercial cultivar 'Metallic Mist' U.S. Plant Pat. No. 19,567 in most horticultural characteristics. However, 'Little Moon' differs in the following:

1. The new cultivar has more colorful foliage.
2. The new cultivar is more tolerant of heat and humidity.
3. The new cultivar is more root hardy.
4. The new cultivar has a smaller leaf size.
5. The new cultivar has a smaller flower size.
6. Plants of the new cultivar are smaller.

BRIEF DESCRIPTION OF THE PHOTOGRAPHS

Figure 1:
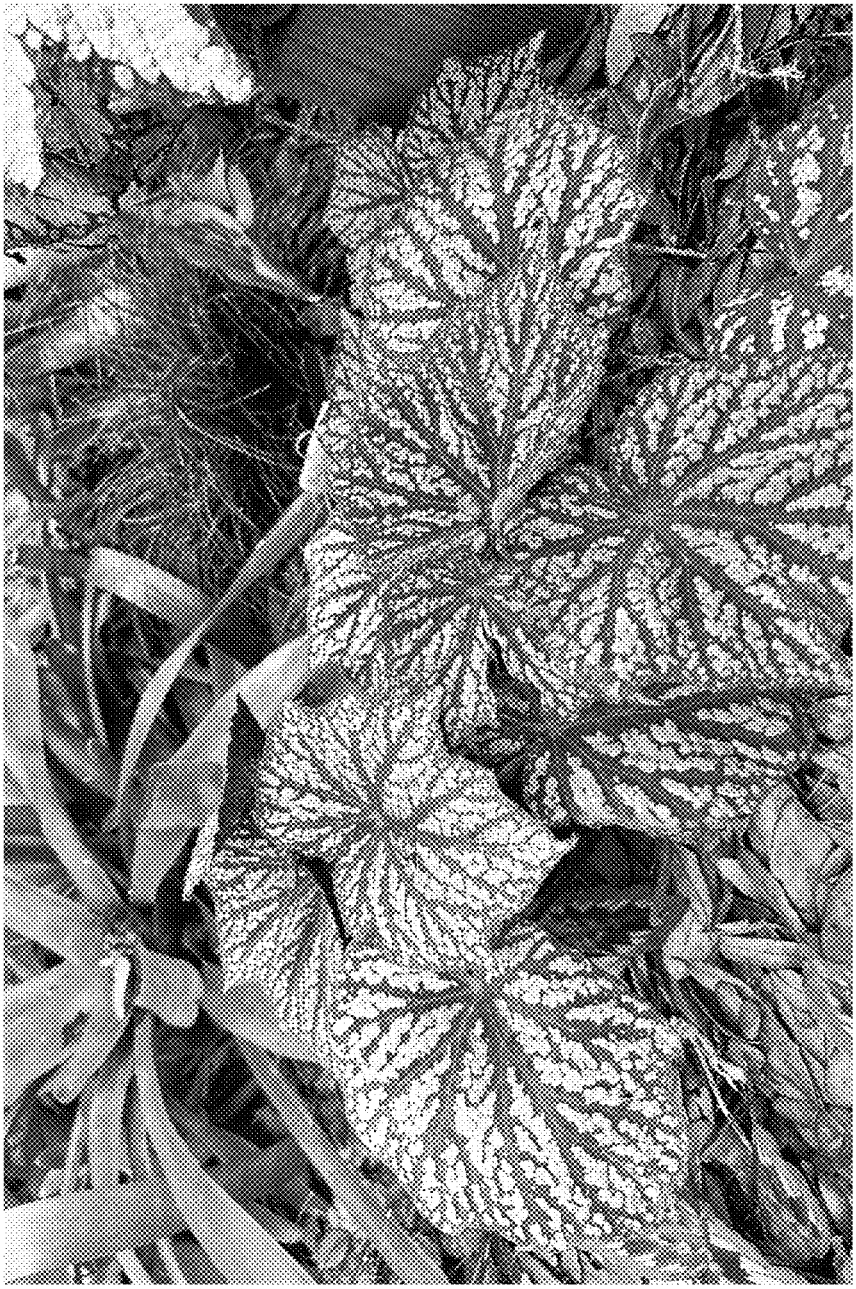

The accompanying photograph in FIG. 1 illustrates in full color a typical plant of 'Little Moon' grown outdoors in Mobile, Alabama. This plant is approximately 1 year old, planted in a shady location in the ground. The photograph is taken from a side view.

Figure 2:
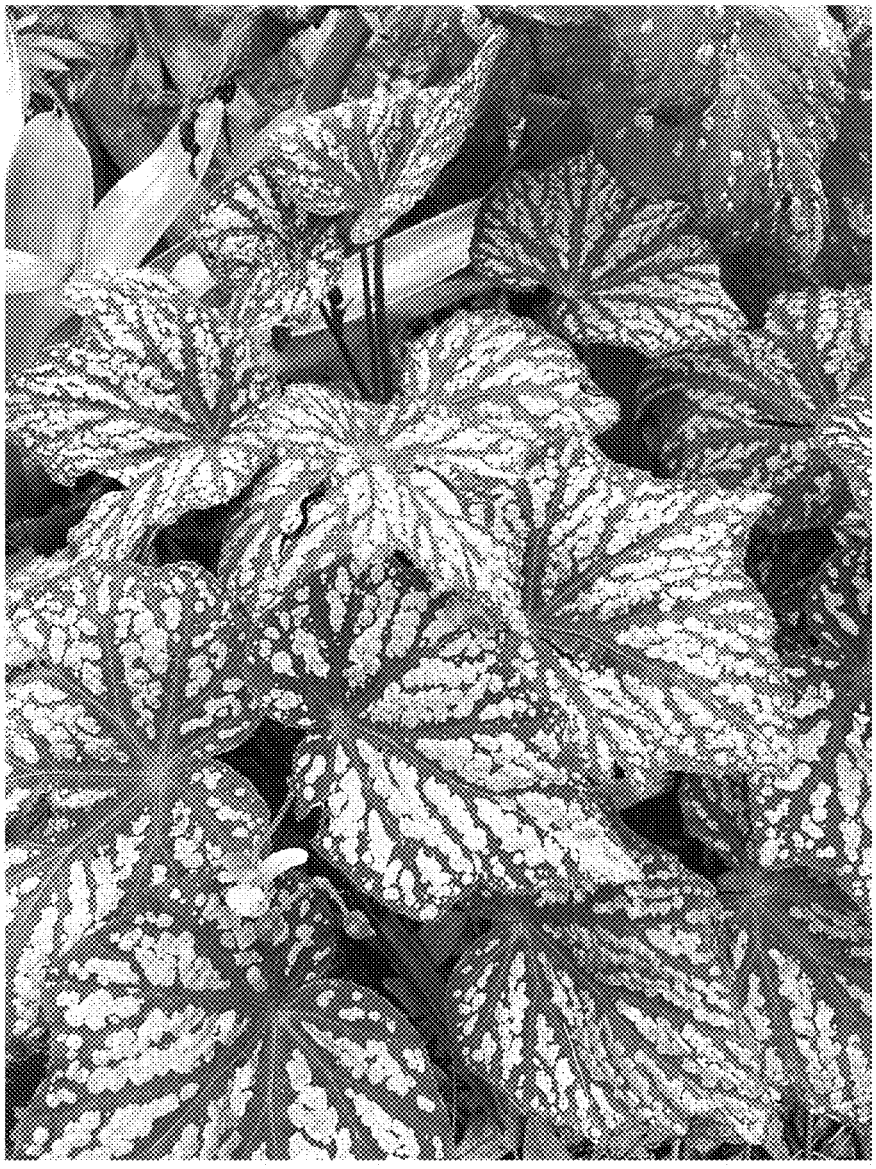

FIG. 2 illustrates the same plant as in FIG. 1, photographed from a top view.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'Little Moon' plants grown in a shade house in Mobile, Alabama during Summer. Temperatures ranged from a low temperature about 55° F. at night to a high around 90° C. during the day. No artificial light, photoperiodic treatments or chemical treatments were given to the plants. Measurements and numerical values represent 16 averages of typical plant types.

Botanical classification: *Begonia* hybrid 'Little Moon'.

Age of the plant described: Approximately 1 year.

Container size of the plant described: 1-gallon commercial container.

PROPAGATION

Typically reproduced commercially by tissue culture. Leaf cutting propagation is also possible.

PLANT

Growth habit: Rhizomatous, spreading, tender perennial.

Pot size of plant described: 1-gallon

Height: Mature plants about 18 to 28 cm.

Plant spread: Mature plants about 30 cm.

Growth rate: Moderate.

Branching characteristics: Leaf petioles emerging from rhizomes. No true branches.

Characteristics of rhizomes:

*Diameter.*—8 to 16 mm.

*Length.*—About 15 cm in a 1-gallon pot.

*Form.*—Round in cross section.

*Color.*—Near RHS Greyed-Purple 187A.

*Texture.*—Glabrous.

*Strength.*—Moderate, fleshy, not brittle.

Internode length: About 1 cm.

FOLIAGE

Arrangement: Emerging basally in a loose, somewhat irregular rosette.

*Quantity.*—Approximately 12 to 15 on a plant of this age.

*Average length.*—Average range 8 to 10 cm.

*Average width.*—Average range 7 to 9 cm.

*Shape of blade.*—Broad kidney shaped.

*Apex.*—Acute.

*Base.*—Cordate. Not overlapping.

*Margin.*—About 5 shallow lobes with very shallow crenation.

*Texture of top surface.*—Glabrous, leathery.

*Texture of bottom surface.*—Glabrous. Very sparse hirsute hairs along main veins.

*Aspect.*—Slightly puckered, overall flat.

*Color.*—Emerging foliage upper side: Near RHS Greyed-Purple N187D flushed 186D. Veins Greyed-Purple 187A. Emerging foliage under side: Near RHS Greyed-Purple 187B. Young foliage upper side: Near RHS Greyed-Green 189C and 189D. Thick coloration along main veins near Greyed-Green N189B. Faint overall flush near Red-Purple 58D. Young foliage under side: Near RHS Greyed-Green 191A and 191B. Strong coloration along veins Greyed-Purple 183A. Mature foliage upper side: Near RHS Greyed-Green 189D. Thick coloration along main veins near Greyed-Green 189A. Mature foliage under side: Near RHS Greyed-Red 187C.

*Venation.*—Type: Palmate. Venation color upper side: Near RHS Greyed-Purple 185D. Venation color under side: Near RHS Greyed-Purple 185A.

*Petiole.*—Length: Average range 10 to 12 cm. Diameter: 7 to 8 mm. Color: Near RHS Greyed-Purple 184B. Texture: Glabrous. Rarely a hirsute hair about 2 to 3 mm long.

*Stipule description.*—1 or 2 per node, non-fleshy, becoming completely dry and papery before leaves fully expand. Length: Approximately 1.4 cm. Diameter: Approximately 9 mm. Color: Begins near Greyed-Red 185A, turning Greyed-Orange 166D when dry. Texture: Glabrous.

FLOWER

Flowering habit: Continuously flowering during Spring and Summer. Flowering begins in May, on the Gulf Coast of the US.

Inflorescence and flower type and habit: Single flowers arranged in axillary cymes. Cymes held slightly above or within foliage, approximately 2 to 4 flowers per cyme.

Cyme size:

*Diameter.*—Approximately 4 cm.

*Height.*—Approximately 2.5 cm.

Flower longevity on plant: About a week, depending upon environmental conditions.

Persistent or self-cleaning: Self-Cleaning.

Bud:

*Shape.*—Ovate.

*Length.*—Approximately 1.5 cm, including bracts. Tepal bud alone about 1.2 cm.

*Diameter.*—Approximately 1 cm, including bracts. Tepal bud alone about 1.0 cm.

*Color.*—Tepal bud near RHS Red 52A. Immature bracts around bud colored near Red 49C.

Flower size:

*Diameter.*—Approximately 2.5 cm.

*Depth.*—Approximately 2.1 cm, including protruding stamens.

Tepals:

*Quantity.*—Approximately 5.

*Arrangement.*—Rotate.

*Length.*—Approximately 1.4 cm.

*Width.*—Approximately 1.1 cm.

*Shape.*—Ovate.

*Apex.*—Obtuse.

*Base.*—Broad attenuate.

*Margin.*—Entire.

*Aspect.*—Slight upward curve.

*Texture, upper and lower surfaces.*—Matte.

*Appearance, upper and lower surfaces.*—Slightly iridescent.

*Color.*—When opening, upper surface: Near RHS Red 55B. When opening, lower surface: Near RHS Red 55A streaked 55A. Fully opened, upper surface: Near RHS Red 56D streaked 55D. Fully opened, lower surface: Near RHS Red 56D streaked 55B.

Flower bracts:

*Quantity per flower.*—2.

*Shape.*—Ovate, strongly concave.

*Length.*—Approximately 2.0 cm.

*Diameter*.—Approximately 1.1 cm, when manually flattened.
*Apex*.—Acute.
*Base*.—Truncate.
*Margin*.—Entire.
*Texture*.—Glabrous.
*Aspect*.—Strongly curved inward towards tepals.
*Color*.—Near RHS Red 52B when mature. Immature bracts near Red 49B.

Peduncles:
*Length*.—Average range 9 to 16 cm.
*Diameter*.—Approximately 4 mm.
*Angle*.—About 15° to the rhizome.
*Strength*.—Moderate, flexible.
*Texture*.—Glabrous.
*Color*.—Near RHS Greyed-Purple 185D.

Pedicels:
*Length*.—Approximately 2.5 cm.
*Diameter*.—Approximately 3 mm.
*Angle*.—About 45° to the peduncle.
*Strength*.—Moderate, flexible.
*Texture*.—Glabrous.
*Color*.—Near RHS Red-Purple 58C.

Fragrance: None.

REPRODUCTIVE ORGANS

Stamens:
*Number*.—8, arising from staminoidal column.

Anthers:
*Description*.—Fleshy, curly.
*Length*.—Free portion about 7 mm.
*Color*.—Near RHS Green-Yellow 1C.
*Pollen*.—Scant to none. Colored near Yellow 4C.

Pistil:
*Number*.—1.
*Length*.—Approximately 1 cm.
*Style*.—Length: Approximately 2 mm. Color: Near RHS Yellow-Green 145B.
*Stigma*.—Shape: Linear. Color: Near RHS Yellow-Green 145D. Ovary Color: Near RHS Yellow-Green 145B.

OTHER CHARACTERISTICS

Seeds: Not observed.

Disease/pest resistance: Moderate resistance and susceptibility to common diseases and pests of *Begonia* have been observed in the new cultivar.

Temperature tolerance: USDA Zone 7-9.

What is claimed is:

1. A new and distinct cultivar of *Begonia* plant named 'Little Moon' as herein illustrated and described.

* * * * *